United States Patent
Phukan et al.

(10) Patent No.: US 9,200,119 B2
(45) Date of Patent: Dec. 1, 2015

(54) SILICON-CONTAINING ZWITTERIONIC LINEAR COPOLYMER COMPOSITION

(71) Applicant: Momentive Performance Materials Inc., Albany, NY (US)

(72) Inventors: Monjit Phukan, Bangalore (IN); Anubhav Saxena, Bangalore (IN); Ravikumar Kodagahally, Bangalore (IN); Mark Leatherman, Elmsford, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 70 days.

(21) Appl. No.: 13/673,094

(22) Filed: Nov. 9, 2012

(65) Prior Publication Data

US 2014/0134126 A1    May 15, 2014

(51) Int. Cl.
*C08G 77/26* (2006.01)
*C08G 77/392* (2006.01)
*A61K 8/898* (2006.01)
*A61K 8/899* (2006.01)
*A61Q 5/00* (2006.01)
*C08G 77/388* (2006.01)
*A61Q 19/00* (2006.01)
*C08L 83/10* (2006.01)
*C08L 83/12* (2006.01)
*C08G 77/452* (2006.01)
*C08G 77/46* (2006.01)

(52) U.S. Cl.
CPC ............. *C08G 77/392* (2013.01); *A61K 8/898* (2013.01); *A61K 8/899* (2013.01); *A61Q 5/00* (2013.01); *A61Q 19/00* (2013.01); *C08G 77/388* (2013.01); *C08L 83/10* (2013.01); *C08L 83/12* (2013.01); *C08G 77/452* (2013.01); *C08G 77/46* (2013.01)

(58) Field of Classification Search
CPC .. C08G 77/392; C08G 77/388; C08G 77/395; A61K 8/898; A61K 8/899; A61Q 5/00
USPC ............................................ 528/28; 524/262
See application file for complete search history.

(56) References Cited

U.S. PATENT DOCUMENTS

| | | |
|---|---|---|
| 5,807,956 A | 9/1998 | Czech |
| 6,074,654 A | 6/2000 | Drechsler et al. |
| 6,475,568 B1 | 11/2002 | Czech |

FOREIGN PATENT DOCUMENTS

| | | |
|---|---|---|
| DE | 34 17 912 C1 | 7/1985 |
| DE | 10 2005 051587 A1 | 5/2007 |
| EP | 0 276 114 A2 | 7/1988 |
| EP | 0535596 A1 | 4/1993 |
| GB | 1 381 953 A | 1/1975 |
| WO | 01/57048 A1 | 8/2001 |
| WO | 2009/085297 A2 | 7/2009 |
| WO | 2009/085300 A2 | 7/2009 |
| WO | 2010/147779 A2 | 12/2010 |
| WO | 2012/104349 A1 | 8/2012 |
| WO | 2012/143371 A1 | 10/2012 |
| WO | 2013/070306 A1 | 5/2013 |

OTHER PUBLICATIONS

Kollmeier, H.J. et al., "Organo-Polysiloxan Copolymer", Goldschmidt Informiert, Goldschmidt, Essen, De, vol. 4, No. 63, 1984, pp. 41-48, XP002363824, ISSN: 0340-8507.
EPO Communication Relating to the Results of the Partial International Search, which is an Annex to the Invitation to Pay Additional Fees dated Jan. 31, 2014.
Snow et al., "Synthesis and characterization of zwitterionic silicone sulfobetaine surfactants", Langmuir, American Chemical Society, NY, NY; vol. 6, No. 2, 1990, pp. 385-391, XP002428884.

*Primary Examiner* — Kuo-Liang Peng
(74) *Attorney, Agent, or Firm* — Joseph S. Ostroff

(57) ABSTRACT

A silicon-containing copolymer which includes zwitterionic linking groups with the general structures —$N^+(Y^-)(Z)$— or —$N(Z^*)$— and repeating groups which can be divalent silicone moieties, divalent hydrocarbons or divalent polyethers. The copolymer can be used in personal care products, fertilizers and other agricultural products, pesticides, antifouling agents, and various waterborne coating formulations.

26 Claims, No Drawings

SILICON-CONTAINING ZWITTERIONIC LINEAR COPOLYMER COMPOSITION

BACKGROUND

1. Field of the Invention

The present invention relates to modified silicones or silanes and more particularly to silicon-containing linear copolymers which include multiple zwitterionic groups.

2. Background of the Art

Non-hydrolysable linear organo-polysiloxanes are known in prior art. U.S. Pat. No. 5,807,956 describes $(AB)_n$ A type polyorganosiloxane materials with alternating polysiloxane and amino-polyalkylene oxide copolymers. U.S. Pat. No. 6,475,568 teaches organo polysiloxane composition with randomly distributed polysiloxane and polyalkyleneoxide units linked by amine linkages. However they do not describe any zwitterionic modifications of the materials.

Zwitterionic silicones are known in prior art as well. For example DE3417912 teaches short chain polysiloxane composition with the general formula $M(CH_2)_{12}C(O)NH(CH_2)_y N^+(R)_2(CH_2)_zCOO^-$, where M is a polysiloxane polymer; y=2 to 4, z=1 to 3 and R is an alkyl radical with 1 to 4 carbon atoms.

U.S. Pat. No. 4,496,705 teaches polyorganosiloxane copolymer with degree of polymerization about 800 for use in elastomers.

EP276114 describes simple polydimethylsiloxane with sulfobetaine groups attached as pendants and/or at the ends of the siloxane chains.

SUMMARY

Modified silicones can exhibit a variety of physical properties. The polymers can be modified to be hydrophilic, lipophilic and hydrophobic depending on the nature of the organic substituents. Recently, linear alternating copolymers and linear random copolymers with zwitterionic groups have been made using alkyl and/or polyether, and polysiloxane units. These materials have shown unexpected and superior properties as surface modifying agents in fiber treatment, antistatic additive and coating additives.

According to the invention, there is provided silicon-containing linear copolymers comprising zwitterionic linking groups with the general structures:

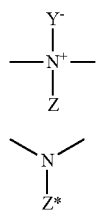

wherein:
Y⁻ is an anionic radical, independently chosen from
—$(CR^1R^2)_bCOO^-$,
—$(CR^3R^4)_cSO^{3-}$,
and
—$(CR^5R^6)_dP(O)(OR^7)O^-$,
wherein $R^1$, $R^2$, $R^3$, $R^4$, $R^5$, $R^6$ and $R^7$ are independently selected from hydrogen, monovalent organic radical containing 1 to 60 carbon atoms and may contain heteroatoms. The subscript b can be 1 to 60, c can be 3 to 60 and d can be 3 to 60;

Z is a monovalent radical independently chosen from—
a) an organic radical containing 1 to 200 carbon atoms and may contain heteroatoms,
b) hydrogen,
and
c) an organosilicone radical given by:

$$M_e M^A_f M^S_g M^D_h D_i D^D_j T_k T^D_l Q_o \quad (III)$$

wherein
$M=R^8R^9R^{10}SiO_{1/2}$,
$M^A=R^{11}R^{12}R^{13}SiR^{14}$,
$M^S=R^{15}_p(R^{16}O)_q SiR^{17}$,
$M^D=R^{18}R^{19}R^{20}SiO_{1/2}$,
$D=R^{21}R^{22}SiO_{2/2}$,
$D^D=R^{23}R^{24}SiO_{2/2}$,
$T=R^{25}SiO_{3/2}$,
$T^D=R^{26}SiO_{3/2}$ and
$Q=SiO_{4/2}$ where:
$R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;
$R^{11}$, $R^{12}$, $R^{13}$, $R^{15}$ and $R^{16}$ are independently selected from the group of monovalent hydrocarbon radicals having 1-20 carbons;
$R^{14}$, $R^{17}$, $R^{20}$ and $R^{26}$ are linear or branched divalent radicals containing 1 to 60 carbon atoms and may contain heteroatoms;
the subscript f is 0 or 1 subject to the limitation if h is 1 then e+g+i+j+k+l+o=0; the subscripts e, g, h, i, j, k, l and o are zero or positive and have values ranging from about 0 to 10;
the subscripts p and q are zero or positive subject to the limitation that if g is positive p+q=3;
Z* is a monovalent zwitterionic group with the general structure

—$XN^+(R^{27}R^{28})Y^-$, wherein:
X is a linear, cyclic or branched divalent organic radical with 2 to 20 carbon atoms and optionally containing heteroatoms,
$R^{27}$ and $R^{28}$ are monovalent radicals with 1 to 20 carbon atoms and optionally having heteroatoms.

The repeating units of the linear copolymer backbone comprise:
a) a linear divalent silicone moiety comprising of the general structure:

$$R^{29}\{Si(R^{30}R^{31})O\}_a SiR^{32}R^{33}R^{34},$$

wherein:
$R^{29}$ and $R^{34}$ are divalent branched or linear organic radicals containing 1 to 60 carbon atoms and may contain heteroatoms;
$R^{30}$, $R^{31}$, $R^{32}$ and $R^{33}$ are monovalent organic radicals containing 1 to 200 carbon atoms and may contain heteroatoms and subscript a is a positive number ranging from 1 to 500; or,
b) a divalent hydrocarbon radical containing linear, branched or cyclic alkyl, aryl, aralkyl hydrocarbon radical of 1 to 200 carbons; or
c) a divalent polyether having the formula:

$$R^{35}O(C_2H_4O)_w(C_3H_6O)_x(C_4H_8O)_y R^{36}$$

wherein:

$R^{35}$ and $R^{36}$ are independently a divalent hydrocarbon radical containing one or more heteroatoms and having from 2 to 20 carbon atoms, the subscript w is zero or positive and has a value ranging from 0 to about 200, the subscript x is zero or positive and has a value ranging from 0 to about 200 and the subscript y is zero or positive and has a value ranging from 0 to about 200 such that (w+x+y)>0.

In a preferred embodiment of the current invention the groups $R^1$, $R^2$, $R^3$, $R^4$, $R^5$, $R^6$ and $R^7$ are independently selected from hydrogen, monovalent organic radical containing 1 to 6 carbon atoms and may contain heteroatoms; the subscript b can be 1 to 6, c can be 3 to 6 and d can be 3 to 6.

In one embodiment of the present invention is a block copolymer with the general structure:

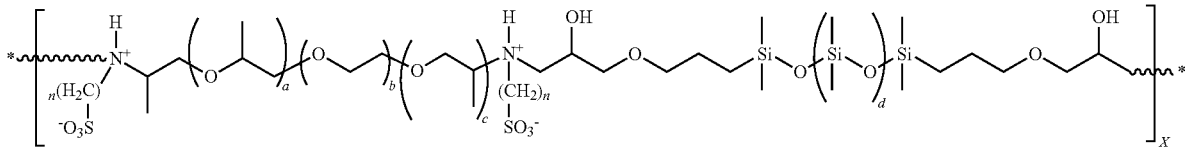

where: a+c is greater than 1, a is greater than or equal to 0, b is greater than or equal to 0, n is 3 to 6, d is 0 to about 500 and X is greater than 1.

In another embodiment of the present invention is a random copolymer with the structure:

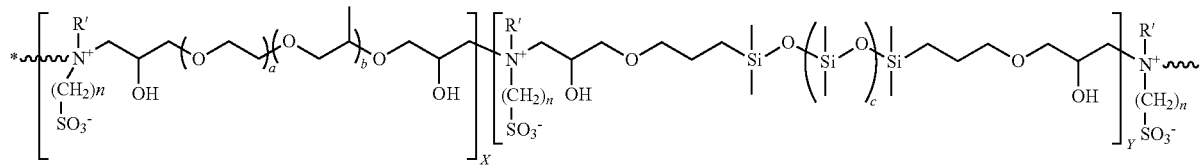

where: a is 0 to about 100, b is 0 to about 100, c is 0 to about 500, X is greater than or equal to zero and Y is greater than equal to zero such that X+Y is greater than zero. R' is independently selected from an alkyl radical with 1 to 20 carbon atoms, may contain heteroatoms such as 0, halogens; it can also be silicon-containing group comprising the structures: —R"Si(OSiR$_3$)$_3$, —R"Si(OSiR$_3$)$_2$R, —R"Si(OSiR$_3$)R$_2$, —R"Si(OR)$_3$, —R"Si(OR)$_2$R, —R"Si(OR)R$_2$ with R being a monovalent hydrocarbon radical with 1 to 20 carbon atoms, optionally having hetero atoms and R" is a divalent hydrocarbon radical with 2 to 20 carbon atoms, optionally with heteroatoms. The above random copolymer structure is subject to the limitation that: if Y is zero then at least one of R' is an aforementioned silicon containing group.

In yet another embodiment of the present invention is a random copolymer with the structure:

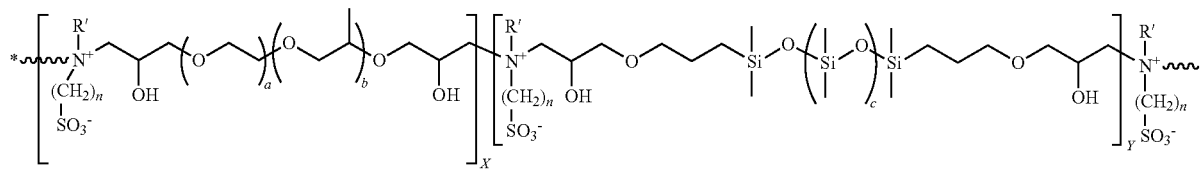

where: a is 0 to about 100, b is 0 to about 100, c is 0 to about 500, X is greater than or equal to zero and Y is greater than zero. R' is independently selected from hydrogen, an alkyl radical with 1 to 20 carbon atoms, a polyether containing radical with the structure: —R"O($C_2H_4O$)$_u$($C_3H_6O$)$_v$($C_4H_8O$)$_w$Z wherein: R" is a divalent hydrocarbon radical with 2 to 20 carbon atoms, optionally with heteroatoms; u+v+w is 1 to about 200 and Z is hydrogen or a monovalent radical with 1 to 10 carbon atoms, may contain heteroatoms.

DETAILED DESCRIPTION OF PREFERRED EMBODIMENT(S)

In the specification and claims herein, the following terms and expressions are to be understood as indicated.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g., a pigment. Additional reactive components may also be added; such components may react with the initial reactants or they may react with the reaction product; the phrase "reaction product" is intended to include those possibilities as well as including the addition of non-reactive components.

Other optional ingredients may be added in the compositions of the present invention including coupling agents, e.g., silane coupling agents, curing aids, e.g., activators, retarders and accelerators, processing additives such as oils, plasticizers, tackifying resins, silicas, other fillers, pigments, fatty acids, zinc oxide, waxes, antioxidants and anti-ozonants, peptizing agents, reinforcing materials such as, for example, carbon black, and so forth. Such additives are selected based upon the intended use and such selection is within the knowledge of one of skill in the art, as are the required amounts of such additives known to one of skill in the art.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

The compositions of the present invention can be used commercially as a demulsifying agents, in agricultural compositions including fertilizers, in cosmetics and personal care products, in household cleaners, in coating compositions such as waxes and the like, in water processing apparatuses as well as other products.

According to the invention, there is provided silicon-containing linear copolymers comprising zwitterionic linking groups with the general structures:

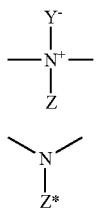

(I)

(II)

wherein:

$Y^-$ is an anionic radical, independently chosen from
—$(CR^1R^2)_b COO^-$,
—$(CR^3R^4)_c SO^{3-}$,
and
—$(CR^5R^6)_d P(O)(OR^7)O^-$,
wherein $R^1$, $R^2$, $R^3$, $R^4$, $R^5$, $R^6$ and $R^7$ are independently selected from hydrogen, monovalent organic radical containing 1 to 60 carbon atoms and may contain heteroatoms. The subscript b can be 1 to 60, c can be 3 to 60 and d can be 3 to 60.

In a preferred embodiment of the current invention the groups $R^1$, $R^2$, $R^3$, $R^4$, $R^5$, $R^6$ and $R^7$ are independently selected from hydrogen, and a monovalent organic radical containing 1 to 6 carbon atoms and may contain heteroatoms; the subscript b can be 1 to 6, c can be 3 to 6 and d can be 3 to 6.

Z of formula (I) is a monovalent radical independently chosen from—
  a) an organic radical containing 1 to 200 carbon atoms and may contain heteroatoms,
  b) hydrogen and
  c) an organosilicone radical given by:

$$M_e M^A_f M^S_g M^D_h D_i D^D_j T_k T^D_l Q_o$$ (III)

wherein
$M = R^8 R^9 R^{10} SiO_{1/2}$,
$M^A = R^{11} R^{12} R^{13} SiR^{14}$,
$M^S = R^{15}_p (R^{16}O)_q SiR^{17}$,
$M^D = R^{18} R^{19} R^{20} SiO_{1/2}$,
$D = R^{21} R^{22} SiO_{2/2}$,
$D^D = R^{23} R^{24} SiO_{2/2}$,
$T = R^{25} SiO_{3/2}$,
$T^D = R^{26} SiO_{3/2}$ and
$Q = SiO_{4/2}$ where:

$R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;

$R^{11}$, $R^{12}$, $R^{13}$, $R^{15}$ and $R^{16}$ are independently selected from the group of monovalent hydrocarbon radicals having 1-20 carbons;

$R^{14}$, $R^{17}$, $R^{20}$ and $R^{26}$ are linear or branched divalent radicals containing 1 to 60 carbon atoms and may contain heteroatoms;

the subscript f is 0 or 1 subject to the limitation if h is 1 then e+g+i+j+k+l+o=0; the subscripts e, g, h, i, j, k, l and o are zero or positive and have values ranging from about 0 to 10;

the subscripts p and q are zero or positive subject to the limitation that if g is positive p+q=3;

$Z^*$ of formula (II) is a monovalent zwitterionic group with the general structure

—$XN^+(R^{27}R^{28})Y^-$, wherein:

X is a linear, cyclic or branched divalent organic radical with 2 to 20 carbon atoms and optionally containing heteroatoms, $R^{27}$ and $R^{28}$ are monovalent radicals with 1 to 20 carbon atoms and optionally having heteroatoms.

The repeating units of the linear copolymer backbone comprise:

a) a linear divalent silicone moiety comprising of the general structure:

$$R^{29}\{Si(R^{30}R^{31})O\}_a SiR^{32}R^{33}R^{34},$$

wherein:

$R^{29}$ and $R^{34}$ are divalent branched or linear organic radicals containing 1 to 60 carbon atoms and may contain heteroatoms;

$R^{30}$, $R^{31}$, $R^{32}$ and $R^{33}$ are monovalent organic radicals containing 1 to 200 C atom and may contain heteroatoms and a is a positive number ranging from 1 to 500; and/or b) a divalent hydrocarbon radical containing linear, branched or cyclic alkyl, aryl, aralkyl hydrocarbon radical of 1 to 200 carbons; and/or c) a divalent polyether having the formula:

$$R^{35}O(C_2H_4O)_w(C_3H_6O)_x(C_4H_8O)_y R^{36}$$

wherein:

$R^{35}$ and $R^{36}$ are independently a divalent hydrocarbon radical containing one or more heteroatoms and having from 2 to 20 carbon atoms, the subscript w is zero or positive and has a value ranging from 0 to about 200, the subscript x is zero or positive and has a value ranging from 0 to about 200 and the subscript y is zero or positive and has a value ranging from 0 to about 200 such that (w+x+y)>0.

In one embodiment of the present invention is a block copolymer with the general structure:

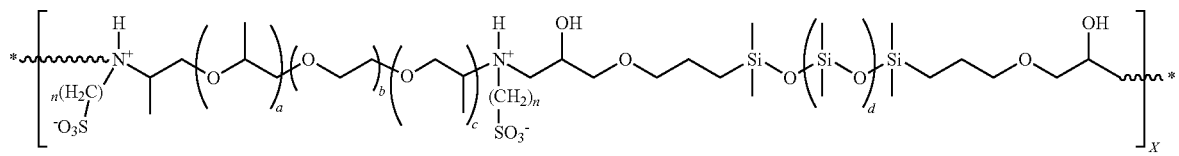

wherein subscript a is from 0 to 200, subscript c is from 0 to 200 such that a+c is greater than 1, a is greater than equal to zero, b is greater than or equal to 0, n is 3 to 6, d is 0 to about 500 and X is greater than 1.

In another embodiment of the present invention is a random copolymer with the structure:

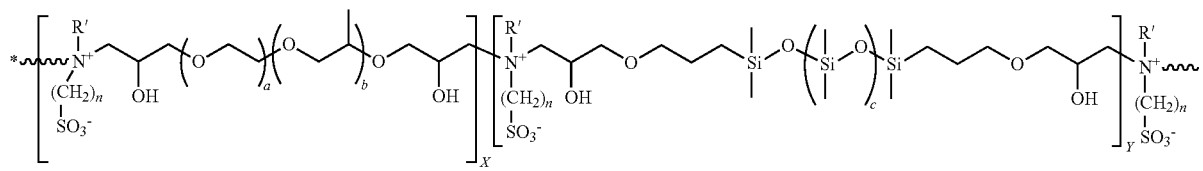

where: a is 0 to about 100, b is 0 to about 100, c is 0 to about 500, X is greater than or equal to zero and Y is greater than equal to zero such that X+Y is greater than one. R' is independently selected from an alkyl radical with 1 to 20 carbon atoms, may contain heteroatoms such as 0, halogens; it can also be silicon containing group comprising of the structures: —R"Si(OSiR$_3$)$_3$, —R"Si(OSiR$_3$)$_2$R, —R"Si(OSiR$_3$)R$_2$, —R"Si(OR)$_3$, —R"Si(OR)$_2$R, —R"Si(OR)R$_2$, with R being a monovalent hydrocarbon radical with 1 to 20 carbon atoms, optionally having hetero atoms and R" is a divalent hydrocarbon radical with 2 to 20 carbon atoms, optionally with heteroatoms. The above random copolymer structure is subject to the limitation that: if Y is zero then at least one of R' is an aforementioned silicon containing group.

In yet another embodiment of the present invention is a random copolymer with the structure:

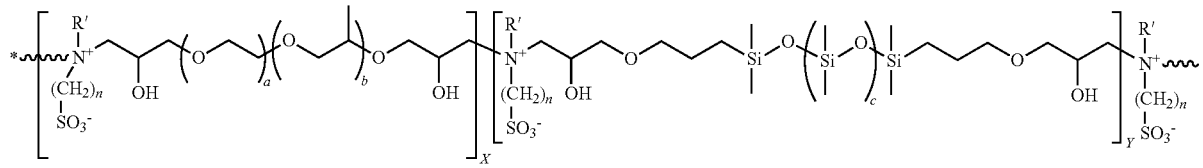

where: a is 1 to about 100, b is 0 to about 100, c is 0 to about 500, X is greater than or equal to zero and Y is greater than zero. R' is independently selected from hydrogen, an alkyl radical with 1 to 20 carbon atoms, and a polyether containing radical with the structure: —R"O(C$_2$H$_4$O)$_u$(C$_3$H$_6$O)$_v$(C$_4$H$_8$O)$_w$Z wherein: R" is a divalent hydrocarbon radical with 2 to 20 carbon atoms, optionally with heteroatoms; u+v+w is 1 to about 200 and Z is hydrogen or a monovalent radical with 1 to 10 carbon atoms, and may contain heteroatoms.

The ionic silicone copolymer compositions of the present invention are suitable for many applications in which the known advantageous properties of the silicones and the properties that could be derived from the ionic groups are important, preferably in the fields of healthcare, personal care, agriculture, automobile, electronics/electrical, aerospace, fuel cells, production of domestic appliances, machine and instrument construction, coatings, membranes and adhesives, and can be employed in waterborne coating formulations.

Silicones have extensively been used in healthcare applications because of their unique film forming ability, which can provide high oxygen permeability, superior smoothness and greater comfort to the wearer. However, due to the lack of the hydrophilicity and water-absorbing property of the silicones, their applications in wound care are very limited (e.g., as backing layer for low exuding wound and scar management). In the wound care industry, there is a growing interest in the development of wound dressings that possess functionality beyond providing physical protection and an optimal moisture environment for the wound. To this end, a dressing material based on a sulfonated tri-block polymer has been reported. This sulfonated polymer possesses an ion-exchange capability that is amenable to binding and controlled release of a variety of therapeutic agents and offers several advantages over existing commercial hydrogels used as wound dressings. These include: (1) excellent film forming properties, (2) hydrophilicity that is proportional to sulfonation level, (3) easy preparation of fabric supported dressings (e.g., polyester, cotton, nylon), (4) excellent mechanical integrity of the materials when hydrated, and (5) stability to a variety of sterilization methodologies. However, synthetic polymers comprised of organic moieties often lack the degree of flexibility or plasticity that is desired for application to a skin surface that it is in constant movement. Materials derived from ionic silicones deliver unique benefits of silicones such as high oxygen permeability and comfort along with high moisture transmission, controlled release of active agents, e.g., silver, antibiotics, growth factors, peptides, proteins and polysaccharides like heparin for the wound care applications.

In addition, the silicone copolymers of the invention can also be used for drug delivery applications. Silicones have a long tradition of being used for drug delivery through a wide variety of routes of administration such as transdermal (silicone gels and adhesive films for delivery of anti-inflammatories, analgesics, steroids, hormones and as smoking-cessation devices), mucosal (elastomer rings and plugs for vaginal delivery of contraceptives, anti-viral agents, anti-fungal agents). However, only relatively hydrophobic drugs can be delivered through the silicone matrix. Hydrophilic active agents have been found to slowly crystallize, which reduces their activity and alters the delivery profile of the device. The ionic silicone copolymer compositions of the present invention, on account of their hydrophilicity can prevent this unwanted crystallization of the drug. Additionally, many drugs can be loaded as bound to the ionic moieties within the silicones, which may further reduce their potential to crystallize and de-activate, thereby increasing shelf-life. Examples of pharmaceutically active ingredients that can be included within the composition include but are not limited to bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, hormone analogs, enzymes, proteins and peptides, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and their combinations thereof.

The composition comprising the above ingredients can be utilized for numerous healthcare applications comprising of drug delivery systems, transdermal patches, wound healing patches, wound dressing patches, transdermal iontophoresis, scaffold for tissue engineering, anti-microbial devices, wound management devices, ophthalmic devices, bioinserts, prostheses and body implants.

The ionic silicone copolymer compositions of the present invention can be used in control release fertilizer applications, the coatings of these copolymers act as barrier to water-soluble constituents of the fertilizers, shielding them from premature release in aqueous environments for a long period of time. The benefits obtained by the use of these coatings can include labor savings, increased crop yield, increased nitrogen utilization efficiently and time savings. The silicone copolymer compositions of the invention can be made to form highly flexible elastomeric films that are devoid of any defects or cracks. Examples of fertilizers and agricultural agents that can be incorporated within zwitterionic silicone copolymenr films include but are not limited to: urea, urea ammonium nitrogen, zinc sulfate, ferrous sulfate, ammonium thiosulfate, potassium sulfate, monoammonium phosphate, urea phosphate, calcium nitrate, phosphoric acid, magnesium hydroxide, manganese carbonate, calcium polysulfide, manganese sulfate, calcium chloride, diammonium phosphate, disodium phosphate, monoammonium phosphate, monopotassium phosphate, sodium hexametaphosphate, sodium tripolyphosphate, tetrapotassium pyrophosphate, trisodium phosphate, tetrasodium pyrophosphate, oxides/sulfates of Zn, Mn, Fe, Cu, Mg, boron, boric acid, potassium and sodium salts of boric acid, and sodium molybdate.

Seed coatings, which usually contain an agricultural agent, pesticide, fungicide or other active ingredients and film-forming polymer to hold the active ingredients on the seed, are commonly applied to the surface of the seeds to protect them from various microbial and insecticidal activities. The desirable properties of the polymers used in the seed coatings are that they: (a) adhere effectively to the seed surface while providing the uniform coatings, (b) result in a flexible and non-tacky coating with high degree of tear and abrasion resistance, (c) render the coating permeable to moisture, oxygen, visible light, carbon dioxide, and (d) allow the films to retain and release various active ingredients over a prolonged period. Various prior cross-linked organic polymers used as a film former in the prior art for seed coating applications mainly include the cross-linked copolymer of acrylics, modified polyacrylamide and vinyl acrylic resins or the copolymers of polyvinyl acetate, methyl cellulose, etc. However, most of these coatings suffer from the following drawbacks: (a) they are not permeable to gases, (b) they have poor ability to control rate of release of ingredients, and (c) at low temperature (especially in winter season) the coating has a tendency to form discontinuous films which exhibit cracking and flaking. Seed coatings comprising silicone polymers address many of the problems associated with traditional organic coatings. However, due to the strongly hydrophobic nature of the silicone polymers, the active ingredients, which are mostly hydrophilic in nature, are not compatible with the films and hence can easily get separated out from the films. However, due to the presence of zwitterionic groups the functionalized ionic silicone composition provided herein can deliver the unique film forming benefits of silicones along with the sustained release of actives. The ionic silicone is a novel class of material, which exhibits the unique benefits of silicones with a controllable extent of hydrophilicity and can be used in seed coating applications. Thus, examples of some agents that can be incorporated in seed coatings include pesticides. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds. Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like, imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl. Insecticide, larvacide, miticide and ovacide compounds that can be used with the composition of the present invention include, but are not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The polymer functionalized with anionic groups such as sulfonate, sulfate, carboxylate or phosphate groups can ionically bind basic nitrogen-containing biocides and these polymer-biocide bonds are almost irreversible and very stable in non-polar solvents. In water, however the interaction is weaker and exhibits a larger degree of reversibility. Therefore, when these polymer films are exposed to water, the biocide molecules in the surface layer dissociate and desorbs from the polymer. This unique combination of properties, make these materials highly attractive for antifouling paint applications where slow and sustained release of the biocide ingredients is an essential requirement. Organic polymers functionalized with different anionic groups can be used in antifouling paint applications which show improved performance with respect to the distribution and fixation of the biocide in the paint matrix. Although silicone-based paints offer some benefits including resistance to heat and weathering, water repellency, superior smoothness etc., which are not available from the organic polymers-based paints, use of the ionically modified silicone copolymer composition of the invention achieves superior distribution and fixation of the biocides in the paint while retaining the benefits of silicone. Examples of antifouling agents that can be incorporated within the composition include, but are not limited to: metal ions such as copper, silver, zinc, tin, organotin compounds, cationic agents such as chlorhexidine, poly(hexamethylene biguanide), Tralopyril, zinc pyrithione, copper thiocyanate, copper(I)oxide, Dichlofluanid, copper pyrithione, 4,5-dichloro-2-octyl-2H-isothiazole-3-on, benzalkonium chloride, or Zineb.

The functionalized ionic silicone composition of the present invention can also be utilized in personal care for providing transfer resistance, moisturization and control delivery of various personal care ingredients.

The ionic groups of the present invention are hydrophilic in nature, and the films formed from these compositions have high flexibility on account of them being polyorganosiloxanes. Because of this unique combination of properties, these compositions can provide the flexibility to develop personal care formulations along that has the advantages of high transfer resistance, gloss, comfort, and control delivery of actives.

The personal care formulations comprising of the present composition can contain surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, hormone analogs, enzymes, proteins and peptides, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, thickening agents, particulate fillers, silicones, clays, plasticizers, occlusives, sensory enhancers, esters, resins, film formers, film forming emulsifiers, high refractive index materials and their combinations thereof.

Further, the personal care compositions comprising of the present invention can find application as antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprises at least one of the foregoing applications.

The examples 1, 3, 5 and 7 are comparative examples and examples 2, 4, 6 and 8 are examples according to current invention.

SYNTHETIC EXAMPLES

Example 1

In a three-necked round bottom flask equipped with a thermometer, a condenser and an addition funnel, 77 g of a polyether amine with average molecular formula $H_2NCH(CH_3)CH_2(OCH_2CH(CH_3))_x(OCH_2CH_2)_y(OCH_2CH(CH_3))_zNH_2$ with x+z=6 and y=12.5 were taken. To this 100 ml of isopropyl alcohol (IPA), 0.1% of titanium isopropoxide catalyst were added and stirred at 60° C. to homogenize the mix. This was followed by slow addition of 123 g of epoxy end-capped siloxane with average molecular formula $CH_2(O)CHCH_2O(CH_2)_3SiO(CH_3)_2SiO(CH_3)_2)_{18}Si(CH_3)_2(CH_2)_3OCH_2CH(O)CH_2$ dissolved in 100 ml of IPA. The solution was heated to reflux and stirred with a mechanical stirrer and was held at the reflux temperature until all the epoxy groups were consumed, as determined by titration. The resulting material exhibited a straw color. The material was transferred to a rotary evaporator and stripped at 70° C. and 4 Torr for 2 hr to remove the isopropanol. A viscous liquid was obtained.

Example 2

The Silicone amino polyether from example 1 (100 g), 1,4-butane sultone (14 g) and IPA (50 g) were combined in a 500 mL round bottom flask. The solution was heated to reflux and stirred with a mechanical stirrer. The reaction was allowed to remain at reflux until all the amine groups were consumed as determined by titration. The resulting material exhibited a dark straw color. The material was transferred to a rotary evaporator and stripped at 70° C. and 4 Torr for 2 hrs to remove the isopropanol. A viscous, clear and straw colored liquid was obtained.

Example 3

In a three-necked round bottom flask equipped with a thermometer, a condenser and an addition funnel, 42.6 g of a polyether amine with average molecular formula $H_2NCH(CH_3)CH_2(OCH_2CH(CH_3))_x(OCH_2CH_2)_y(OCH_2CH(CH_3))_z NH_2$ with x+z=6 and y=12.5 were taken and added 150 ml of IPA & 0.1% of titanium isopropoxide catalyst was added and stirred at 60° C. Then 150 g of epoxy end-capped siloxane with average molecular formula $CH_2(O)CHCH_2O(CH_2)_3SiO(CH_3)_2(SiO(CH_3)_2)_{55}Si(CH_3)_2(CH_2)_3OCH_2CH(O)CH_2$ in 150 ml of IPA was slowly added. The solution was heated to reflux and stirred with a mechanical stirrer. The reaction was allowed to remain at reflux until all the epoxy groups were consumed as determined by titration. The resulting material exhibited a straw color. The material was transferred to a rotary evaporator and stripped at 70° C. and 4 Torr for 2 hr to remove the isopropanol. A viscous liquid was obtained.

Example 4

The Silicone amino polyether from example 3 (40 g), 1,4-butane sultone (2.92 g) and IPA (50 g) were combined in a 250 mL round bottom flask. The solution was heated to reflux and stirred with a mechanical stirrer. The reaction was allowed to remain at reflux until all the amine groups were consumed as determined by titration. The resulting material exhibited a dark straw color. The material was transferred to a rotary evaporator and stripped at 70° C. and 4 Torr for 2 hrs to remove the isopropanol. A viscous, clear and straw colored liquid was obtained.

Example 5

In a three-necked round bottom flask equipped with a thermometer, a condenser and an addition funnel, 53.1 gm of epoxy endcapped siloxane with average molecular formula $CH_2(O)CHCH_2O(CH_2)_3SiO(CH_3)_2(SiO(CH_3)_2)_{55}Si(CH_3)_2(CH_2)_3OCH_2CH(O)CH_2$ and 3.92 gm of epoxy end-capped polyether with the average structure of $CH_2(O)CHCH_2O(CH_2CH_2O)_9CH_2CH(O)CH_2$ in 75 ml of IPA has taken mixed at 60 C for 5 minutes and added 1.35 gm of 2-ethanolamine in 15 ml of IPA and 0.1% of titanium isopropoxide catalyst stirred at 80° C. using mechanical stirrer. The solution was heated to reflux and stirred with a mechanical stirrer. The reaction was allowed to remain at reflux until all the epoxy groups were consumed as determined by titration. The resulting material exhibited a straw color. The material was transferred to a rotary evaporator and stripped at 70° C. and 4 Torr for 2 hrs to remove the isopropanol. A viscous liquid was obtained.

Example 6

The silicone amino polyether from example 5 (50 g), 1,4-butane sultone (9 g) were combined in a 250 mL round bottom flask with 50 g of IPA. The solution was heated to reflux and stirred with a mechanical stirrer. The reaction was allowed to remain at reflux until all the amine groups were consumed as determined by titration. The resulting material exhibited a dark straw color. The material was transferred to a rotary evaporator and stripped at 70° C. and 4 Torr for 2 hrs to remove the isopropanol. A viscous liquid was obtained.

Example 7

In a three-necked round bottom flask equipped with a thermometer, a condenser and an addition funnel, 13.2 gm of a polyether amine with average molecular formula $H_2NCH(CH_3)CH_2(OCH_2CH(CH_3))_x(OCH_2CH_2)_y(OCH_2CH(CH_3))_z NH_2$ with x+z=6 and y=12.5 were taken and added 75 ml of IPA & 0.1% of titanium isopropoxide catalyst was added and stirred at 60° C. Then 100 gm of epoxy endcapped siloxane with average molecular formula $CH_2(O)CHCH_2O(CH_2)_3SiO(CH_3)_2(SiO(CH_3)_2)_{125}Si(CH_3)_2(CH_2)_3OCH_2CH(O)CH_2$ in 75 ml of IPA slowly added. The solution was heated to reflux and stirred with a mechanical stirrer. The reaction was allowed to remain at reflux until all the epoxy groups were consumed as determined by titration. The resulting material exhibited a straw color. The material was transferred to a rotary evaporator and stripped at 70° C. and 4 Torr for 2 hrs to remove the isopropanol. A viscous liquid was obtained.

Example 8

The silicone amino polyether from example 7 (40 g), 1,4-butane sultone (1.75 g) were combined in a 250 mL round bottom flask with 50 g of IPA. The solution was heated to reflux and stirred with a mechanical stirrer. The reaction was allowed to remain at reflux until all the amine groups were consumed as determined by titration. The resulting material exhibited a dark straw color. The material was transferred to a rotary evaporator and stripped at 70° C. and 4 Torr for 2 hrs to remove the isopropanol. A viscous liquid was obtained.

Test Data

Viscosity of the Silicone Polymers

| Silicone Co-polymer | Viscosity (Pa s) |
| --- | --- |
| Example 1 | 598 |
| Example 2 | 5787 |
| Example 3 | 937 |
| Example 4 | 9114 |
| Example 5 | 472 |
| Example 6 | 4422 |
| Example 7 | 6223 |
| Example 8 | Hard Film |

Solubility of the Sulfobetaine Modified Polymers

| Material | 0.5 wt % in Water | 0.5 wt % in IPA | 0.5 wt % in IDD | 0.5 wt % in Hexane |
| --- | --- | --- | --- | --- |
| Example 2 | D | S | I | I |
| Example 4 | D | S | I | I |
| Example 6 | D | S | I | I |
| Example 8 | I | S | I | I |

Note:
S = Soluble,
I = Insoluble,
D = Dispersible,
IDD = isododecane

Textile Treatment Formulations

| Ingredients | Amount |
| --- | --- |
| Example 8 | 20% |
| TDE-3 (Tridecyl alcohol + 3EO) | 5% |
| Di-propylene glycol | 10% |
| Water | 55% |

With the formulation provided above microemulsion for textile treatment were prepared as described: Example 8, TDE-3 and di-propyleneglycol were mixed in a reactor with overhead stirrer at 700-800 rpm for 10 min. After that stirring was stopped, 30% water was added and stirred again for 15 min to give a whitish viscous mass. Then 10% water was added gradually and mixed for another 15 mins. Finally remaining 15% water was added and continued mixing for 15 min and stirring was stopped. This yields a clear microemulsion that can be applied to textiles for improving softening after dilution in water to 1 to 20%.

Hair Care Application

Material of example 8 was dissolved in IDD to make a 5% solution. 1 ml of this was then applied to a 10 inch platinum bleached hair trace and allowed to stand for 5 min. After this the trace was washed with copious amount of water and dried using a hair drier. The resultant hair trace was visibly shiny and hand feel was smooth compared to that without treatment.

| | Mass (g) | | |
| --- | --- | --- | --- |
| Ingredients | CF1 | CF2 | F1 |
| SE30 (PDMS Gum) Momentive Performance Materials | 2.5 | 1 | — |
| Example 8 | — | — | 1 |
| SR1000 (Silicone Resin) Momentive Performance Materials | — | 1.5 | 1.5 |
| Bentone Gel VS-5 PC V (Thickener) Elementis Specialties Inc. | 0.81 | 0.81 | 0.81 |
| IDD (Solvent) Presperse LLC | 4 | 4 | 4 |
| Red Shade Dispersion "GE" (Pigment) International Foodcraft Corp. | 2.4 | 2.4 | 2.4 |
| TiO2-MT100 TV (Pigment) Tri-K Industries | 0.29 | 0.29 | 0.29 |

In the table above, CF1 and CF2 are the control lip colour formulations with low and high transfer resistance. These are prepared by mixing all the ingredients in Flack-tack high speed mixer.

Transfer Resistance Measurement

The transfer resistance measurements were carried out using the method described in U.S. Pat. No. 6,074,654 with the following exceptions. Each formulation was individually applied to an artificial skin films (pre-hydrated over 30% aqueous glycerin solution for 24 h) and dried at 40° C. The films were then subjected a rubbing insult using a tester device. A 500 g mass was covered with a piece of white cotton knit cloth. The assemble was place on the surface of the coated in vitro skin. The assembly was rotated 360°. The cloth was then electronically imaged and the percent area darkened by the red lip formulation transferred was determined by image processing software. The higher the coverage of transfer the more lip formulation transferred from the coated in vitro skin to the white cloth. This process was repeated on the same location of in vitro skin. Each rotation (360°) of the abrasive surface across the dried film was counted as one "insult". The highest limit of transfer coverage is considered to be 100%, which means the entire abrasive surface is covered by colored material. Lower transfer coverage is indicative of better transfer resistance.

| | CF1 | CF2 | F1 |
| --- | --- | --- | --- |
| Insult 1 | 100 | 79% | 51% |
| Insult 2 | 47% | 42% | 46% |
| Insult 3 | 19% | 24% | 54% |
| Insult 4 | 44% | 25% | 55% |
| Insult 5 | 48% | 9% | 53% |

Tack Measurements on In Vitro Skin

The in vitro skin was prepared in the same manner as the above examples. Once the formulation was dried on the in vitro skin, the tack-force of the dried films were measure using Dia-Stron (MTT 175) instrument, Higher the tack-force, lesser is the tackiness of the composition.

| Tack Force (gmf) | CF2 | F1 |
| --- | --- | --- |
| Reading 1 | 49.7 | 0.3 |
| Reading 2 | 51.85 | 0.35 |
| Reading 3 | 52.15 | 0.4 |
| Reading 4 | 52.65 | 0.35 |
| Reading 5 | 54.05 | 0.75 |
| Average | 52.08 ± 1.57 | 0.43 ± 0.18 |

Gloss Measurement

The in vitro skin was prepared in the same manner as the above examples. Once the formulation was dried on the in vitro skin, the gloss (at 60 degree angle) of the dried films was measured using BYK-Gardner Gloss Meter Instrument.

| | CF2 | F1 |
| --- | --- | --- |
| Gloss (GU) | 6.5 | 16.8 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A silicon-containing linear copolymer comprising repeating units in a backbone of the copolymer and at least one zwitterionic linking group linking units in the backbone of the copolymer, the linking group having the general structures:

(I)

(II)

wherein:
Y⁻ is an anionic radical, independently chosen from:
—$(CR^1R^2)_bCOO^-$,
—$(CR^3R^4)_cSO^{3-}$,
and
—$(CR^5R^6)_dP(O)(OR^7)O^-$,
wherein:
$R^1, R^2, R^3, R^4, R^5, R^6$ and $R^7$ are independently selected from hydrogen, monovalent organic radical containing 1 to 60 carbon atoms and may contain heteroatoms, the subscript b is 1 to 60, c is 3 to 60 and d is 3 to 60;

Z of formula (I) is a monovalent radical independently chosen from:
a) organic radical containing 1 to 200 carbon atoms and may contain heteroatoms,
b) hydrogen, and
c) an organosilicone radical given by—

$$M_eM^A_fM^S_gM^D_hD_iD^D_jT_kT^D_lQ_o \qquad (III)$$

wherein
$M=R^8R^9R^{10}SiO_{1/2}$,
$M^A=R^{11}R^{12}R^{13}SiR^{14}$,
$M^S=R^{15}_p(R^{16}O)_qSiR^{17}$,
$M^D=R^{18}R^{19}R^{20}SiO_{1/2}$,
$D=R^{21}R^{22}SiO_{2/2}$,
$D^D=R^{23}R^{24}SiO_{2/2}$,
$T=R^{25}SiO_{3/2}$,
$T^D=R^{26}SiO_{3/2}$ and
$Q=SiO_{4/2}$;
where
$R^8, R^9, R^{10}, R^{18}, R^{19}, R^{21}, R^{22}, R^{23}, R^{24}$ and $R^{25}$ are each independently selected from the group of monovalent hydrocarbon radicals having from 1 to 60 carbon atoms, may optionally contain heteroatoms;
$R^{11}, R^{12}, R^{13}, R^{15}$ and $R^{16}$ are independently selected from the group of monovalent hydrocarbon radicals having 1-20 carbons;
$R^{14}, R^{17}, R^{20}$ and $R^{26}$ are linear or branched divalent radicals containing 1 to 60 carbon atoms and may contain heteroatoms;
the subscript f is 0 or 1 subject to the limitation if h is 1 then e+g+i+j+k+l+o=0,
the subscripts e, g, h, i, j, k, and l are zero or positive and have values ranging from about 0 to 10,
the subscripts p and q are zero or positive subject to the limitation that if g is positive p+q=3;
Z* of formula (II) is a monovalent zwitterionic group with the general structure

—$XN^+(R^{27}R^{28})Y^-$, wherein
X is a divalent organic radical with 2 to 20 carbon atoms and optionally containing heteroatoms,
$R^{27}$ and $R^{28}$ are monovalent radicals with 1 to 20 carbon atoms and optionally having heteroatoms.

2. The copolymer of claim 1 wherein the repeating units comprise a silicone moiety with the general structure:

$$R^{29}\{Si(R^{30}R^{31})O\}_aSiR^{32}R^{33}R^{34};$$

wherein:
$R^{29}$ and $R^{34}$ are divalent branched or linear organic radicals containing 1 to 60 carbon atoms and may contain heteroatoms;
$R^{30}, R^{31}, R^{32}$ and $R^{33}$ are monovalent organic radicals containing 1 to 200 C atom and may contain heteroatoms and a is a positive number ranging from 1 to 500.

3. The copolymer of claim 1 wherein the repeating units comprise a divalent hydrocarbon radical containing linear, branched or cyclic alkyl, aryl, aralkyl hydrocarbon radical of 1 to 200 carbons.

4. The copolymer of claim 1 wherein the repeating units comprise a divalent polyether having the formula:

$$R^{35}O(C_2H_4O)_w(C_3H_6O)_x(C_4H_8O)_yR^{36}$$

where
$R^{35}$ and $R^{36}$ are independently a divalent hydrocarbon radical containing one or more heteroatoms and having from 2 to 20 carbon atoms,
the subscript w is zero or positive and has a value ranging from 0 to about 200,
the subscript x is zero or positive and has a value ranging from 0 to about 200 and
the subscript y is zero or positive and has a value ranging from 0 to about 200 such that (w+x+y)>0.

5. The copolymer of claim 1 wherein the Z group comprises a silicone moiety with the structure:

$$M_eM^A_fM^S_gM^D_hD_iD^D_jT_kT^D_lQ_o$$

with
$M=R^8R^9R^{10}SiO_{1/2}$,
$M^A=R^{11}R^{12}R^{13}SiR^{14}$,
$M^S=R^{15}_p(R^{16}O)_qSiR^{17}$,
$M^D=R^{18}R^{19}R^{20}SiO_{1/2}$,
$D=R^{21}R^{22}SiO_{2/2}$,
$D^D=R^{23}R^{24}SiO_{2/2}$,
$T=R^{25}SiO_{3/2}$,
$T^D=R^{26}SiO_{3/2}$ and
$Q=SiO_{4/2}$;
where
$R^8, R^9, R^{10}, R^{18}, R^{19}, R^{21}, R^{22}, R^{23}, R^{24}$ and $R^{25}$ are each independently selected from the group of monovalent hydrocarbon radicals having from 1 to 60 carbon atoms, may optionally contain heteroatoms;
$R^{11}, R^{12}, R^{13}, R^{15}$ and $R^{16}$ are independently selected from the group of monovalent hydrocarbon radicals having 1-20 carbons; $R^{14}, R^{17}, R^{20}$ and $R^{26}$ are linear or branched divalent radicals containing 1 to 60 carbon atoms and may contain heteroatoms;
the subscript f is 0 or 1 subject to the limitation if h is 1 then e+g+i+j+k+l+o=0;
the subscripts e, g, h, i, j, k, and l are zero or positive and have values ranging from about 0 to 10;
the subscripts p and q are zero or positive subject to the limitation that if g is positive p+q=3.

6. The copolymer of claim 1 wherein the groups $R^8, R^9, R^{10}, R^{11}, R^{12}, R^{13}, R^{15}, R^{16}, R^{18}, R^{19}, R^{21}, R^{22}, R^{23}, R^{24}, R^{25}, R^{30}, R^{31}, R^{32}$ and $R^{33}$ are independently selected from methyl, ethyl, propyl, isopropyl, phenyl and fluoro-containing hydrocarbons.

7. The copolymer of claim 1 comprising the structure:

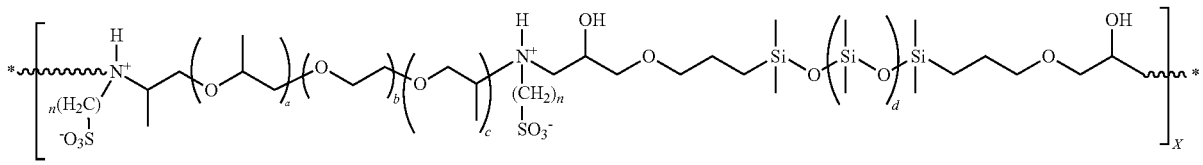

where: a+c is greater than 1, a is greater than or equal to 0, b is greater than or equal to 0, n is 3 to 6, d is 0 to about 500 and X is greater than 1.

8. The copolymer of claim 1 comprising the structure:

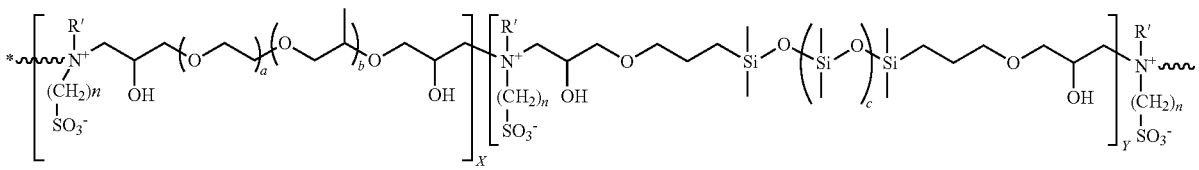

where: a is 0 to about 100, b is 0 to about 100, c is 0 to about 500, X is greater than or equal to zero and Y is greater than equal to zero such that X+Y is greater than one, R' is independently selected from the group consisting of an alkyl radical with 1 to 20 carbon atoms which may contain heteroatoms, —R"Si(OSiR$_3$)$_3$, —R"Si(OSiR$_3$)$_2$R, —R"Si(OSiR$_3$)R$_2$, —R"Si(OR)$_3$, —R"Si(OR)$_2$R and —R"Si(OR)R$_2$, wherein R is a monovalent hydrocarbon radical with 1 to 20 carbon atoms and optionally having hetero atoms, and R" is a divalent hydrocarbon radical with 2 to 20 carbon atoms, optionally with heteroatoms, with the proviso that if Y is zero then at least one of R' is a silicon containing group.

9. The copolymer of claim 1 comprising a random copolymer of the following general structure:

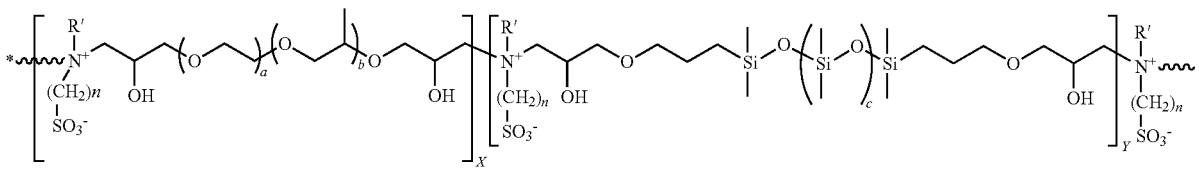

where: a is 0 to about 100, b is 0 to about 100, c is 0 to about 500, X is greater than or equal to zero and Y is greater than zero, R' is independently selected from hydrogen, an alkyl radical with 1 to 20 carbon atoms and a polyether-containing radical with the structure $$—R"O(C_2H_4O)_u(C_3H_6O)_v(C_4H_8O)_wZ$$

wherein: R" is a divalent hydrocarbon radical with 2 to 20 carbon atoms, optionally with heteroatoms; u+v+w is 1 to about 200 and Z is hydrogen or a monovalent radical with 1 to 10 carbon atoms and may contain heteroatoms.

10. A composition comprising a silicon-containing linear copolymer and at least one active agent
wherein the linear copolymer comprises repeating units in a backbone of the copolymer and at least one zwitterionic linking group linking units in the backbone of the copolymer, the linking group having the general structures:

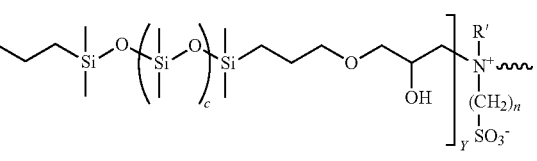

wherein:

$Y^-$ is an anionic radical, independently chosen from:
—$(CR^1R^2)_bCOO^-$,
—$(CR^3R^4)_cSO^{3-}$,
and
—$(CR^5R^6)_dP(O)(OR^7)O^-$, wherein:

$R^1$, $R^2$, $R^3$, $R^4$, $R^5$, $R^6$ and $R^7$ are independently selected from hydrogen, monovalent organic radical containing 1 to 60 carbon atoms and may contain heteroatoms, the subscript b is 1 to 60, c is 3 to 60 and d is 3 to 60;

Z of formula (I) is a monovalent radical independently chosen from:

a) organic radical containing 1 to 200 carbon atoms and may contain heteroatoms, b) hydrogen, and c) an organosilicone radical given by—

$$M_eM^A_fM^S_gM^D_hD_iD^D_jT_kT^D_lQ_o \qquad (III)$$

wherein $M=R^8R^9R^{10}SiO_{1/2}$, $M^A=R^{11}R^{12}R^{13}SiR^{14}$, $M^S=R^{15}{}_p(R^{16}O)_qSiR^{17}$, $M^D=R^{18}R^{19}R^{20}SiO_{1/2}$, $D=R^{21}R^{22}SiO_{2/2}$, $D^D=R^{23}R^{24}SiO_{2/2}$, $T=R^{25}SiO_{3/2}$, $T^D=R^{26}SiO_{3/2}$ and $Q=SiO_{4/2}$;

where $R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;

$R^{11}$, $R^{12}$, $R^{13}$, $R^{15}$ and $R^{16}$ are independently selected from the group of monovalent hydrocarbon radicals having 1-20 carbons;

$R^{14}$, $R^{17}$, $R^{20}$ and $R^{26}$ are linear or branched divalent radicals containing 1 to 60 carbon atoms and may contain heteroatoms;

the subscript f is 0 or 1 subject to the limitation if h is 1 then e+g+i+j+k+l+o=0, the subscripts e, g, h, i, j, k, and l are zero or positive and have values ranging from about 0 to 10, the subscripts p and q are zero or positive subject to the limitation that if g is positive p+q=3;

Z* of formula (II) is a monovalent zwitterionic group with the general structure

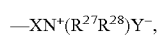
—XN⁺(R²⁷R²⁸)Y⁻, wherein

X is a divalent organic radical with 2 to 20 carbon atoms and optionally containing heteroatoms, $R^{27}$ and $R^{28}$ are monovalent radicals with 1 to 20 carbon atoms and optionally having heteroatoms.

11. The composition of claim 10 wherein the composition is a personal care formulation and the at least one active agent is selected from the group consisting of anti-fungal agents, medicinal compounds, biological extracts, hormones, enzymes, anti-bacterial agents and growth regulators for personal care applications.

12. A personal care formulation comprising a silicon-containing linear copolymer and one or more of surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, thickening agents, particulate fillers, silicones, clays, plasticizers, occlusives, sensory enhancers, esters, resins, film formers, film forming emulsifiers and high refractive index materials wherein the linear copolymer comprises repeating units in a backbone of the copolymer and at least one zwitterionic linking group linking units in the backbone of the copolymer, the linking group having the general structures:

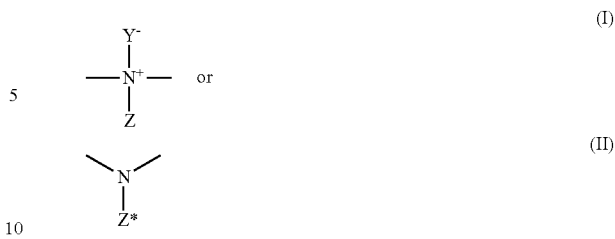

wherein:

Y⁻ is an anionic radical, independently chosen from:

—(CR¹R²)ₐCOO⁻,

—(CR³R⁴)ₑSO³⁻, and

—(CR⁵R⁶)ₐP(O)(OR⁷)O⁻, wherein:

$R^1$, $R^2$, $R^3$, $R^4$, $R^5$, $R^6$ and $R^7$ are independently selected from hydrogen, monovalent organic radical containing 1 to 60 carbon atoms and may contain heteroatoms, the subscript b is 1 to 60, c is 3 to 60 and d is 3 to 60;

Z of formula (I) is a monovalent radical independently chosen from:

a) organic radical containing 1 to 200 carbon atoms and may contain heteroatoms, b) hydrogen, and c) an organosilicone radical given by—

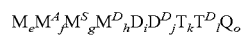
$M_eM^A{}_fM^S{}_gM^D{}_hD_iD^D{}_jT_kT^D{}_lQ_o$ (III)

wherein $M=R^8R^9R^{10}SiO_{1/2}$, $M^A=R^{11}R^{12}R^{13}SiR^{14}$, $M^S=R^{15}{}_p(R^{16}O)_qSiR^{17}$, $M^D=R^{18}R^{19}R^{20}SiO_{1/2}$, $D=R^{21}R^{22}SiO_{2/2}$, $D^D=R^{23}R^{24}SiO_{2/2}$, $T=R^{25}SiO_{3/2}$, $T^D=R^{26}SiO_{3/2}$ and $Q=SiO_{4/2}$;

where $R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;

$R^{11}$, $R^{12}$, $R^{13}$, $R^{15}$ and $R^{16}$ are independently selected from the group of monovalent hydrocarbon radicals having 1-20 carbons;

$R^{14}$, $R^{17}$, $R^{20}$ and $R^{26}$ are linear or branched divalent radicals containing 1 to 60 carbon atoms and may contain heteroatoms;

the subscript f is 0 or 1 subject to the limitation if h is 1 then e+g+i+j+k+l+o=0, the subscripts e, g, h, i, j, k, and l are zero or positive and have values ranging from about 0 to 10, the subscripts p and q are zero or positive subject to the limitation that if g is positive p+q=3;

Z* of formula (II) is a monovalent zwitterionic group with the general structure

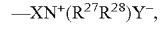
—XN⁺(R²⁷R²⁸)Y⁻, wherein

X is a divalent organic radical with 2 to 20 carbon atoms and optionally containing heteroatoms, $R^{27}$ and $R^{28}$ are monovalent radicals with 1 to 20 carbon atoms and optionally having heteroatoms.

13. The composition of claim 11 wherein the personal care formulation is an antiperspirant/deodorants, shaving product, skin lotion, moisturizer, toner, bath product, cleansing product, shampoo, conditioner, combined shampoo/conditioner, mousse, styling gel, hair spray, hair dye, hair color product, hair bleach, waving product, hair straightener, nail polish, nail polish remover, nail cream, nail lotions, cuticle softener, sunscreen, insect repellent, anti-aging product, lipstick, cosmetic foundation, face powder, eye liner, eye shadow, blush, makeup, mascara, body and hand preparation, skin care preparation, face and neck preparation, tonic, dressing, hair grooming aid, aerosol fixative, fragrance preparation, aftershave, soft focus application, non-coloring hair preparation, tanning preparation, synthetic and non-synthetic soap bar, hand liquid, nose strip, non-woven application for personal care, baby lotion, baby bath and shampoos, baby conditioner, shaving cream, cucumber slices, skin pad, make-up remover, facial cleansing product, cold cream, spritz, paste mask and mud, face mask, cologne, toilet waters, hair cuticle coat, shower gel, face and body wash, personal care rinse-off product, foam bath, scrubbing cleanser, astringent, nail conditioner, eye shadow stick, powder for face or eye, lip balm, lip gloss, pump spray, non-aerosol spray, hair-frizz-control gel, hair leave-in conditioner, hair pomades, hair de-tangling product, hair fixative, hair bleach product, skin lotion, pre-shave, anhydrous cream and lotion, oil/water emulsion, water/oil emulsion, multiple and macro and micro emulsion, water-resistant creams and lotion, anti-acne preparation, mouth-wash, massage oil, toothpaste, clear gel and stick, ointment base, topical wound-healing product, aerosol talc, barrier spray, vitamin and anti-aging preparation, herbal-extract preparation, bath salt, bath and body milk, hair styling aid, hair-, eye-, nail- and skin-soft solid application, controlled-release personal care products, hair conditioning mist, skin care moisturizing mist, skin wipe, pore cleaner, blemish reducer, skin exfoliator, skin desquamation enhancer, skin towelette and cloth, depilatory preparation, personal care lubricant, nail coloring preparation, or drug delivery systems for topical application of medicinal compositions that are to be applied to the skin.

14. The composition of claim 10 wherein said composition is a pesticide formulation and the active agent is selected from the group consisting of rodenticides, insecticides, miticides, fungicides, antifouling agents and herbicides.

15. The composition of claim 14 wherein the active agent is a herbicide selected from the group consisting of phenoxy acetic acids, phenoxy propionic acids, phenoxy butyric acids, benzoic acids, triazines and s-triazines, substituted ureas, uracils, hentazon, desmedipham, methazole, phenmedipham, pyridate, amitrole, clomazone, fluridone, norflurazone, dinitroanilines, isopropalin, oryzalin, pendimethalin, prodiamnine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben and bipyridylium compounds.

16. The composition of claim 14 wherein the active agent is a fungicide selected from the group consisting of aldimorph, tridemorph, dodemorph, dimethomorph; flusilazol, azaconazole, cyproconazole, epoxiconazole, furconazole, propiconazole, tebuconazole and the like, imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine and metalaxyl.

17. The composition of claim 14 wherein the active agent is an insecticide selected from the group consisting of *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin and cypermethrin.

18. The composition of claim 14 wherein the active agent is an antifouling agent selected from the group consisting of copper ions, silver ions, zinc ions, tin ions, organotin compounds, chlorhexidine, poly(hexamethylene biguanide), Tralopyril, zinc pyrithione, copper thiocyanate, copper(I)oxide, Dichlofluanid, copper pyrithione, 4,5-dichloro-2-octyl-2H-isothiazole-3-on, benzalkonium chloride and Zineb.

19. The composition of claim 10 wherein the composition is an agricultural composition and the active agent is one or more agricultural agent selected from the group consisting of urea, urea ammonium nitrogen, zinc sulfate, ferrous sulfate, ammonium thiosulfate, potassium sulfate, monoammonium phosphate, urea phosphate, calcium nitrate, phosphoric acid, magnesium hydroxide, manganese carbonate, calcium polysulfide, manganese sulfate, calcium chloride, diammonium phosphate, disodium phosphate, monoammonium phosphate, monopotassium phosphate, sodium hexametaphosphate, sodium tripolyphosphate, tetrapotassium pyrophosphate, trisodium phosphate, tetrasodium pyrophosphate, oxides/sulfates of Zn, Mn, Fe, Cu, Mg, boron, boric acid, potassium and sodium salts of boric acid and sodium molybdate.

20. The composition of claim 10 wherein said composition is a seed coating composition, wherein the copolymer of claim 1 is a film forming agent and the active agent is selected from one or both of an agricultural agent and a pesticide.

21. A textile finishing and/or treatment composition comprising a silicon-containing linear copolymer for natural fibers, synthetic fibers and articles made thereof
wherein the linear copolymer comprises repeating units in a backbone of the copolymer and at least one zwitterionic linking group with the general structures:

wherein:
Y⁻ is an anionic radical, independently chosen from:
—(CR¹R²)$_b$COO⁻,
—(CR³R⁴)$_c$SO$_3^-$,
and
—(CR⁵R⁶)$_d$P(O)(OR⁷)O⁻,
wherein:
R¹, R², R³, R⁴, R⁵, R⁶ and R⁷ are independently selected from hydrogen, monovalent organic radical containing 1 to 60 carbon atoms and may contain heteroatoms, the subscript b is 1 to 60, c is 3 to 60 and d is 3 to 60;
Z of formula (I) is a monovalent radical independently chosen from:
a) organic radical containing 1 to 200 carbon atoms and may contain heteroatoms, b) hydrogen, and
c) an organosilicone radical given by—

$$M_e M^A{}_f M^S{}_g M^D{}_h D_i D^D{}_j T_k T^D{}_l Q_o \quad (III)$$

wherein
$M = R^8 R^9 R^{10} SiO_{1/2}$,
$M^A = R^{11} R^{12} R^{13} SiR^{14}$,
$M^S = R^{15}{}_p (R^{16}O)_q SiR^{17}$,
$M^D = R^{18} R^{19} R^{20} SiO_{1/2}$,
$D = R^{21} R^{22} SiO_{2/2}$,
$D^D = R^{23} R^{24} SiO_{2/2}$,
$T = R^{25} SiO_{3/2}$,
$T^D = R^{26} SiO_{3/2}$ and
$Q = SiO_{4/2}$;
where
$R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;
$R^{11}$, $R^{12}$, $R^{13}$, $R^{15}$ and $R^{16}$ are independently selected from the group of monovalent hydrocarbon radicals having 1-20 carbons;
$R^{14}$, $R^{17}$, $R^{20}$ and $R^{26}$ are linear or branched divalent radicals containing 1 to 60 carbon atoms and may contain heteroatoms;
the subscript f is 0 or 1 subject to the limitation if h is 1 then e+g+j+k+l+o 0,
the subscripts e, g, h, i, j, k, and l are zero or positive and have values ranging from about 0 to 10,
the subscripts p and q are zero or positive subject to the limitation that if g is positive p+q=3;
Z* of formula (II) is a monovalent zwitterionic group with the general structure $$-XN^+(R^{27}R^{28})Y^-,$$

wherein
X is a divalent organic radical with 2 to 20 carbon atoms and optionally containing heteroatoms,
$R^{27}$ and $R^{28}$ are monovalent radicals with 1 to 20 carbon atoms and optionally having heteroatoms.

22. A method for imparting durable hydrophilicity and/or softness to a substrate comprising applying to said substrate a composition according to claim 21.

23. The method of claim 22 wherein the substrate is selected from the group consisting of natural fibers, synthetic fibers and non-woven materials.

24. A hard-surface cleaning and/or treatment composition comprising a silicon-containing linear copolymer
wherein the linear copolymer comprises repeating units in a backbone of the copolymer and at least one zwitterionic linking group linking units in the backbone of the copolymer, the linking group having the general structures:

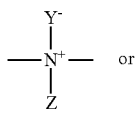

(I)

or

(II)

wherein:
$Y^-$ is an anionic radical, independently chosen from:
$-(CR^1R^2)_b COO^-$,
$-(CR^3R^4)_c SO^{3-}$,
and
$-(CR^5R^6)_d P(O)(OR^7)O^-$,
wherein:
$R^1$, $R^2$, $R^3$, $R^4$, $R^5$, $R^6$ and $R^7$ are independently selected from hydrogen, monovalent organic radical containing 1 to 60 carbon atoms and may contain heteroatoms, the subscript b is 1 to 60, c is 3 to 60 and d is 3 to 60;
Z of formula (I) is a monovalent radical independently chosen from:
a) organic radical containing 1 to 200 carbon atoms and may contain heteroatoms,
b) hydrogen, and
c) an organosilicone radical given by—

$$M_e M^A{}_f M^S{}_g M^D{}_h D_i D^D{}_j T_k T^D{}_l Q_o \quad (III)$$

wherein
$M = R^8 R^9 R^{10} SiO_{1/2}$,
$M^A = R^{11} R^{12} R^{13} SiR^{14}$,
$M^S = R^{15}{}_p (R^{16}O)_q SiR^{17}$,
$M^D = R^{18} R^{19} R^{20} SiO_{1/2}$,
$D = R^{21} R^{22} SiO_{2/2}$,
$D^D = R^{23} R^{24} SiO_{2/2}$,
$T = R^{25} SiO_{3/2}$,
$T^D = R^{26} SiO_{3/2}$ and
$Q = SiO_{4/2}$;
where
$R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;
$R^{11}$, $R^{12}$, $R^{13}$, $R^{15}$ and $R^{16}$ are independently selected from the group of monovalent hydrocarbon radicals having 1-20 carbons;
$R^{14}$, $R^{17}$, $R^{20}$ and $R^{26}$ are linear or branched divalent radicals containing 1 to 60 carbon atoms and may contain heteroatoms;
the subscript f is 0 or 1 subject to the limitation if h is 1 then e+g+i+j+k+l+o=0,
the subscripts e, g, h, i, j, k, and l are zero or positive and have values ranging from about 0 to 10,
the subscripts p and q are zero or positive subject to the limitation that if g is positive p+q=3;
Z* of formula (II) is a monovalent zwitterionic group with the general structure $$-XN(R^{27}R^{28})Y^-,$$

wherein
X is a divalent organic radical with 2 to 20 carbon atoms and optionally containing heteroatoms,
$R^{27}$ and $R^{28}$ are monovalent radicals with 1 to 20 carbon atoms and optionally having heteroatoms.

25. A chemical formulation for hydrocarbon production and processing comprising a silicon-containing linear copolymer
wherein the linear copolymer comprises repeating units in a backbone of the copolymer and at least one zwitterionic linking group linking units in the backbone of the copolymer, the linking group having the general structures:

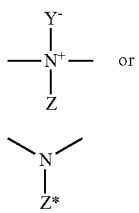
(I)

or (II)

wherein:
$Y^-$ is an anionic radical, independently chosen from:
—$(CR^1R^2)_b COO^-$,
—$(CR^3R^4)_c SO^{3-}$,
and
—$(CR^5R^6)_d P(O)(OR^7)O^-$,
wherein:
$R^1$, $R^2$, $R^3$, $R^4$, $R^5$, $R^6$ and $R^7$ are independently selected from hydrogen, monovalent organic radical containing 1 to 60 carbon atoms and may contain heteroatoms, the subscript b is 1 to 60, c is 3 to 60 and d is 3 to 60;
Z of formula (I) is a monovalent radical independently chosen from:
a) organic radical containing 1 to 200 carbon atoms and may contain heteroatoms,
b) hydrogen, and
c) an organosilicone radical given by—

$$M_e M^A_f M^S_g M^D_h D_i D^D_j T_k T^D_l Q_o \quad (III)$$

wherein
$M = R^8 R^9 R^{10} SiO_{1/2}$,
$M^A = R^{11} R^{12} R^{13} SiR^{14}$,
$M^S = R^{15}{}_p (R^{16}O)_q SiR^{17}$,
$M^D = R^{18} R^{19} R^{20} SiO_{1/2}$,
$D = R^{21} R^{22} SiO_{2/2}$,
$D^D = R^{23} R^{24} SiO_{2/2}$,
$T = R^{25} SiO_{3/2}$,
$T^D = R^{26} SiO_{3/2}$ and
$Q = SiO_{4/2}$;
where
$R^8$, $R^9$, $R^{10}$, $R^{18}$, $R^{19}$, $R^{21}$, $R^{22}$, $R^{23}$, $R^{24}$ and $R^{25}$ are each independently selected from the group of monovalent hydrocarbon radicals having from 1 to 60 carbon atoms, may optionally contain heteroatoms;
$R^{11}$, $R^{12}$, $R^{13}$, $R^{15}$ and $R^{16}$ are independently selected from the group of monovalent hydrocarbon radicals having 1-20 carbons;
$R^{14}$, $R^{17}$, $R^{20}$ and $R^{26}$ are linear or branched divalent radicals containing 1 to 60 carbon atoms and may contain heteroatoms;
the subscript f is 0 or 1 subject to the limitation if h is 1 then e+g+i+j+k+l+o=0,
the subscripts e, g, h, i, j, k, and l are zero or positive and have values ranging from about 0 to 10,
the subscripts p and q are zero or positive subject to the limitation that if g is positive p+q=3;
Z* of formula (II) is a monovalent zwitterionic group with the general structure

—$XN^+(R^{27}R^{28})Y^-$, wherein
X is a divalent organic radical with 2 to 20 carbon atoms and optionally containing heteroatoms,
$R^{27}$ and $R^{28}$ are monovalent radicals with 1 to 20 carbon atoms and optionally having heteroatoms.

26. The chemical formulation of claim 25 selected from the group consisting of demulsifier, anti-foam formulation, anti-corrosion formulation and combinations thereof.

\* \* \* \* \*